United States Patent
Levine et al.

(10) Patent No.: US 6,489,096 B1
(45) Date of Patent: Dec. 3, 2002

(54) QUANTITATIVE ANALYSIS OF HYBRIDIZATION PATTERNS AND INTENSITIES IN OLIGONUCLEOTIDE ARRAYS

(75) Inventors: Arnold J. Levine, Princeton, NJ (US); Uri Alon, Princeton, NJ (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/174,364

(22) Filed: Oct. 15, 1998

(51) Int. Cl.[7] .............................. C12Q 1/68; G06F 19/00
(52) U.S. Cl. .............................................. 435/6; 702/20
(58) Field of Search ........................... 422/50, 68.1, 69, 422/82.05; 435/6, 283.1, 287.1, 287.2, 287.9, 288.7, 289.1; 364/178, 550, 551.01, 825; 702/20

(56) References Cited

U.S. PATENT DOCUMENTS

| | | | |
|---|---|---|---|
| 4,683,202 A | 7/1987 | Mullis | 435/91 |
| 5,143,854 A | 9/1992 | Pirrung et al. | 436/518 |
| 5,206,137 A | 4/1993 | Ip et al. | 435/6 |
| 5,445,934 A | 8/1995 | Fodor et al. | 435/6 |
| 5,492,806 A | 2/1996 | Drmanac et al. | 435/5 |
| 5,498,875 A * | 3/1996 | Obrenski et al. | 250/458.1 |
| 5,525,464 A | 6/1996 | Drmanac et al. | 435/6 |
| 5,571,639 A | 11/1996 | Hubbell et al. | 430/5 |
| 5,593,839 A | 1/1997 | Hubbell et al. | 435/6 |
| 5,653,939 A | 8/1997 | Hollis et al. | 422/50 |
| 5,667,972 A | 9/1997 | Drmanac et al. | 435/6 |
| 5,695,934 A | 12/1997 | Brenner | 435/6 |
| 5,695,940 A | 12/1997 | Drmanac et al. | 435/6 |
| 5,700,637 A * | 12/1997 | Southern | 435/6 |
| 5,707,806 A | 1/1998 | Shuber | 435/6 |
| 5,777,888 A | 7/1998 | Rine et al. | 364/496 |
| 5,795,716 A * | 8/1998 | Chee et al. | 435/6 |
| 5,800,992 A | 9/1998 | Fodor et al. | 435/6 |
| 5,843,767 A | 12/1998 | Beattie | 435/287.1 |
| 5,871,697 A | 2/1999 | Rothberg et al. | 422/68.1 |
| 5,974,164 A | 10/1999 | Chee et al. | 382/129 |
| 6,197,503 B1 * | 3/2001 | Vo-Dink et al. | 435/6 |

FOREIGN PATENT DOCUMENTS

| | | |
|---|---|---|
| EP | 307 476 | 3/1989 |
| EP | 392 546 | 10/1990 |
| EP | 0 235 726 | 5/1993 |
| EP | 0 717 113 | 6/1996 |
| EP | 848 067 | 6/1998 |

(List continued on next page.)

OTHER PUBLICATIONS

Schena et al., Science, vol. 270, pp. 467–470, 1995.*
Adams et al., "Complementary DNA Sequencing: Expressed Sequence Tags and Human Genome Project", *Science*, 252: 1651–1656 (Jun. 21, 1991).

(List continued on next page.)

*Primary Examiner*—Ardin H. Marschel
(74) *Attorney, Agent, or Firm*—Ritter, Lang & Kaplan LLP (57) ABSTRACT

Systems and methods for enhanced quantitative analysis of hybridization intensity measurements obtained from oligonucleotide probes and other probes exposed to target samples are provided by virtue of the present invention. One embodiment ameliorates the effects of high frequency noise superimposed on a hybridization intensity measurement signal measured over successive probe alignments to a target sample sequence. Detection of expressed genes and ESTs and quantitative measurement of expression level may be improved. Mutation detection and base calling may be improved.

6 Claims, 4 Drawing Sheets

FOREIGN PATENT DOCUMENTS

| WO | WO 89/10977 | 11/1989 |
|----|-------------|---------|
| WO | WO 89/11548 | 11/1989 |
| WO | WO 90/15070 | 12/1990 |
| WO | WO 92/10092 | 6/1992 |
| WO | WO 92/10588 | 6/1992 |
| WO | WO 93/22456 | 11/1993 |
| WO | WO 95/11995 | 5/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | WO 97/27317 | 7/1997 |
| WO | WO 97/29212 | 8/1997 |

OTHER PUBLICATIONS

Drmanac, "Sequencing of Megabase Plus DNA by Hybridization: Theory of the Method", *Genomics*, 4:114–128 (1989).

Frickett et al., "Development Of A Database For Nucleotide Sequences", *Mathematical Methods for DNA Sequences*, CRC Press, Ed. Waterman, pp. 2–34 (1989).

Hara et al., "Subtractive cDNA Cloning Using Oligo(dT)$_{30}$–Latex And PCR: Isolation Of cDNA Clones Specific To Undifferentiated Human Embryonal Carcinoma Cells", *Nucleic Acids Res.*, 19(25):7097–7104 (1991).

IntelliGenetics Suite (TM), Release 5.4, Advanced Training Manual, Jan. 1993, published by IntelliGenetics, Inc., 700 Ease El Camino Real, Mountain View, California 94040, USA, pp. (1–6)–(1–19) and (2–9)–(2–14), see entire document.

Khan et al., "Single Pass Sequencing And Physical And Genetic Mapping Of Human Brain cDNAs", *Nat Genet.*, 2:180–185 (1992).

Matsubara et al., "Identification Of New Genes By Systematic Analysis Of cDNAs And Database Construction", *Curr. Opin. Biotechnol.*, 4: 672–677 (1993).

Okubo et al., "Large Scale cDNA Sequencing for Analysis of Quantitative and Qualitative Aspects of Gene Expression", *Nature Genetics*, 2(3):173–179 (1993).

PR Newswire, "Gene Logic to Use Affymetrix GeneChip Arrays to Build Gene Expression Database Products", Jan. 11, 1999.

Gibbs et al., "Detection of Single DNA Base Differences by Competitive Oligonucleotide Priming", *Nucleic Acid Res.*, 17(7):2437–2448 (1989).

Guatelli et al., "Isothermal, In Vitro Amplification of Nucleic Acids by a Multienzyme Reaction Modeled After Retroviral Replication", *Proc. Natl. Acad. Sci. USA*, 87(5):1874–1878 (1990).

Gusella, "DNA Polymorphism and Human Disease", *Annu. Rev. Biochem.*, 55:831–854 (1986).

Kwoh et al., "Transcription–Based Amplification System and Detection of Amplified Human Immunodeficiency Virus Type 1 With a Bead–Based Sandwich Hybridization Format", *Proc. Natl. Acad. Sci. USA*, 86(4):1173–1177 (1989).

Landegren et al., "A Ligase–Mediated Gene Detection Technique", *Science*, 241(4869):1077–1080 (1988).

Mattila et al., "Fidelity of DNA Synthesis by the Thermococcus litoralis DNA Polymerase—An Extremely Heat Stable Enzyme With Proofreading Activity", *Nucleic Acids Res.*, 19(18):4967–4973 (1991).

Orita et al., "Detection of Polymorphisms of Human DNA by Gel Electrophoresis as Single–Strand Conformation Polymorphisms", *Proc. Natl. Acad. Sci. USA*, 86(8):2766–2770 (1989).

Saiki et al., "Analysis of Enzymatically Amplified Beta–Globin and HLA–DQ Alpha DNA with Allele–Specific Oligonucleotide Probes", *Nature*, 324(6093):163–166 (1986).

Wu et al., "The Ligation Amplification Reaction (LAR)—Amplification of Specific DNA Sequences Using Sequential Rounds of Template–Dependent Ligation", *Genomics*, 4(4):560–569 (1989).

Zhao et al., "High–density cDNA filter analysis: a novel approach for large–scale, quantitative analysis of gene expression," *Gene*, 156:207–213 (1995).

\* cited by examiner

QUANTITATIVE ANALYSIS OF HYBRIDIZATION PATTERNS AND INTENSITIES IN OLIGONUCLEOTIDE ARRAYS

BACKGROUND OF THE INVENTION

The present invention relates to computer systems and more particularly to systems and methods for analysis of hybridization of samples to oligonucleotide probes or other polymer probes.

Devices and computer systems for forming and using arrays of materials on a substrate are known. The VLSIPS™ and GeneChip™ technologies provide methods of making and using very large arrays of polymers, such as nucleic acids, on very small chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid). It is also possible to employ other types of probes or probes that are not included in arrays or chips.

Such probes are used for, e.g, base calling, detection of mutations, and analysis of gene expression. For all of these objectives, a typical technique is to expose the probes to target nucleic acid samples that have been marked with fluorescent or otherwise radioactive labels. For each probe or group of probes, a hybridization intensity is determined based on observed fluorescence or radioactivity. The hybridization intensity may also be measured in some other way.

These hybridization intensities are the basis for further analysis including base calling, mutation detection, and evaluation of expression of genes or expressed sequence tags. See European Patent Office Publication No. 0717113A and European Patent Office Publication No. 0848067, the contents of both publications being incorporated herein by reference.

Expression evaluation makes use of hybridization intensities determined from pairs of probes where each pair includes a perfect match probe and a mismatch probe. The term "perfect match probe" refers to a probe that has a sequence that is perfectly complementary to a particular subsequence of a sequence of interest in a target nucleic acid. The term "mismatch control" or "mismatch probe" refer to probes whose sequence is deliberately selected not to be perfectly complementary to a particular target sequence.

For example, to determine the concentration of a particular mRNA sequence indicative of expression of a gene or EST of interest, a series of pairs of perfect match and mismatch probes may be provided. Each pair may include a perfect match probe perfectly complementary to a subsequence of interest. The mismatch probe may differ in one position from the perfect match probe. Each probe may include a series of e.g., 25 bases. The mRNA sequence may be interrogated by a series of probe pairs having successive alignments to the mRNA sequence.

After hybridization intensities are obtained, the number of instances of when the perfect match intensity is greater than the mismatch intensity is obtained, along with the average of the logarithm of the perfect match to mismatch ratios for all the probe pairs. To determine the quantitative abundance of mRNA, the average of the difference between perfect match and mismatch hybridization intensity is also computed.

Further opportunities exist, however, to improve the accuracy of assessments of expression levels. High frequency noise can result from variations in probe alignment to mRNA sequences, causing hybridization intensity to exhibit spurious peaks rather than smooth variation. This high frequency noise is especially prevalent in array designs where there are relatively small number of probes per gene and therefore less opportunity to average out the high frequency noise over results from large number of probes.

What is needed are systems and methods for reducing the deleterious affects of the high frequency noise found in the hybridization intensity measurements.

SUMMARY OF THE INVENTION

Systems and methods for enhanced quantitative analysis of hybridization intensity measurements obtained from oligonucleotide probes and other probes exposed to target samples are provided by virtue of the present invention. One embodiment ameliorates the effects of high frequency noise superimposed on a hybridization intensity signal measured over successive probe alignments to a target sample sequence. Detection of expressed genes and ESTs and quantitative measurement of expression level may be improved. Mutation detection and base calling may be improved.

A nonlinear lowpass filter may be used to remove the effects of spurious peaks in this signal. Also, a hybridization spectrum including the hybridization intensities measured over a series of probes may be compared to a reference hybridization spectrum to obtain a measure of similarity. The measure of similarity may indicate expression or non-expression of a particular gene or EST, or a point mutation.

In accordance with a first aspect of the present invention, a method for analyzing a nucleic acid sequence includes: inputting a plurality of hybridization intensities of probes exposed to the sample nucleic acid sequence, and applying a non-linear filter to the plurality of hybridization intensities.

In accordance with a second aspect of the present invention, a method for analyzing a sample nucleic acid sequence includes: inputting a plurality of hybridization intensities of probes exposed to the sample nucleic acid sequence, the plurality of hybridization intensities forming a hybridization spectrum of the sample nucleic acid sequence, and comparing the hybridization spectrum of the sample nucleic acid sequence to a reference hybridization spectrum to obtain an indication of similarity.

A further understanding of the nature and advantages of the inventions herein may be realized by reference to the remaining portions of the specification and the attached drawings.

DESCRIPTION OF THE SPECIFIC EMBODIMENTS

Figure 1:
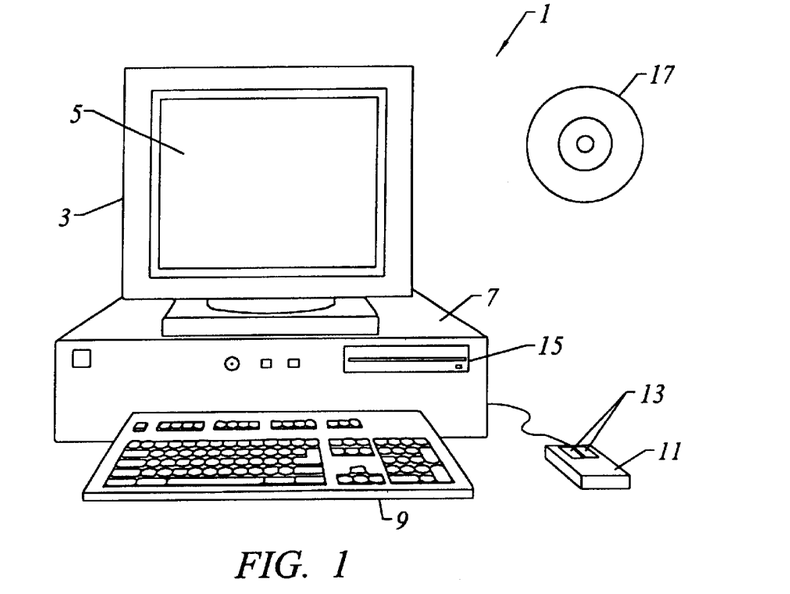
FIG. 1 illustrates an example of a computer system that may be used to execute software embodiments of the present invention.

FIG. 1 illustrates an example of a computer system that may be used to execute software embodiments of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
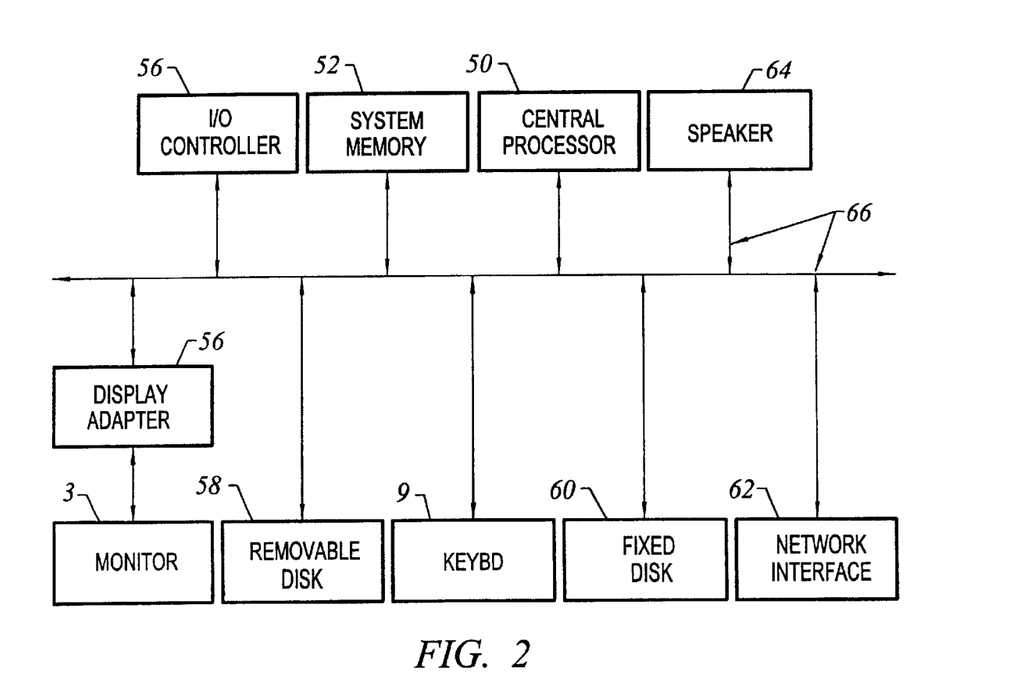
FIG. 2 shows a system block diagram of a typical computer system.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 50, system memory 52, I/O controller 54, display adapter 56, removable disk 58, fixed disk 60, network interface 62, and speaker 64. Removable disk 58 is representative of removable computer readable media like floppies, tape, CD-ROM, removable hard drive, flash memory, and the like. Fixed disk 60 is representative of an internal hard drive or the like. Code to implement aspects of the present invention may be operably disposed in or stored on any type of storage medium.

Other computer systems suitable for use with the present invention may include additional or fewer subsystems. For example, another computer system could include more than one processor 50 (i.e., a multi-processor system) or memory cache.

Arrows such as 66 represent the system bus architecture of computer system 1. However, these arrows are illustrative of any interconnection scheme serving to link the subsystems. For example, display adapter 56 may be connected to central processor 50 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. In one embodiment, the computer system is an IBM compatible personal computer.

The VLSIPS™ and GeneChip™ technologies provide methods of making and using very large arrays of polymers, such as nucleic acids, on very small chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

It should be understood that the probes need not be nucleic acid probes but may also be other polymers such as peptides. Peptide probes may be used to detect the concentration of peptides, polypeptides, or polymers in a sample. The probes must be carefully selected to have bonding affinity to the compound whose concentration they are to be used to measure.

In one embodiment, the present invention provides methods of analyzing information relating to the concentration of compounds in a sample as measured by binding of the compounds to polymers such as polymer probes. In a particular application, the concentration information is generated by analysis of hybridization intensity files for a chip containing hybridized nucleic acid probes. The hybridization of a nucleic acid sample to certain probes may represent the expression level of one more genes or expressed sequence tags (ESTs). The expression level of a gene or EST is herein understood to be the concentration within a sample of mRNA or protein that would result from the transcription of the gene or EST.

Concentration of compounds other than nucleic acids may be analyzed according to one embodiment of the present invention. For example, a probe array may include peptide probes which may be exposed to protein samples, polypeptide samples, or peptide samples which may or may not bond to the peptide probes. By appropriate selection of the peptide probes, one may detect the presence or absence of particular proteins, polypeptides, or peptides which would bond to the peptide probes.

A system that designs a chip mask, synthesizes the probes on the chip, labels nucleic acids from a target sample, and scans the hybridized probes is set forth in U.S. Pat. No. 5,571,639 which is hereby incorporated by reference for all purposes.

The term "perfect match probe" refers to a probe that has a sequence that is perfectly complementary to a particular target sequence. The test probe is typically perfectly complementary to a portion (subsequence) of the target sequence. The term "mismatch control" or "mismatch probe" refer to probes whose sequence is deliberately selected not to be perfectly complementary to a subsequence of a particular target sequence. For each mismatch (MM) control in an array there typically exists a corresponding perfect match (PM) probe that is perfectly complementary to the same subsequence of a particular target sequence.

One possible probe selection strategy is to choose the PM probes to be perfectly complementary to successive subsequences of the target mRNA sequence. For example, the target sequences may be hundreds or thousands of bases long. Each perfect match probe may be 20–45 bases long. For example, in one such scheme, each probe is a 25-mer probe, i.e., the probes are 25 bases long. There may be probe pairs corresponding to every alignment to the target sequence, or there may be, e.g., 2–5 base pair differences in alignment for successive probe pairs. Also, for each alignment used there may be multiple probe pairs.

Hybridization intensities may be obtained by fluorescent scanning. The expression evaluation techniques, described for example in European Patent Office Publication No. 0848067 are based on relative measurements of the hybridization intensities for PM and MM probes. For example, the determination of whether the gene or EST is in fact expressed in the sample may be based on the number of probe pairs where the PM intensity exceeds the MM intensity by a threshold along with the average logarithm of the PM/MM ratios. Other criteria may be the number of probe pairs where both the PM intensity exceeds the MM intensity by a difference threshold or where the PM intensity divided by the MM intensity exceeds a ratio threshold. The quantitative expression level may depend on the average difference between PM and MM intensities. Hybridization intensities are the basis for all of these techniques.

For probe having successive alignments to a target sequence, the hybridization intensity will not typically vary smoothly but will rather exhibit spurious peaks. The present invention provides systems and methods for alleviating the deleterious effects of the peaks. In one embodiment, a nonlinear filter is applied to the hybridization data to remove these peaks.

Figure 3:
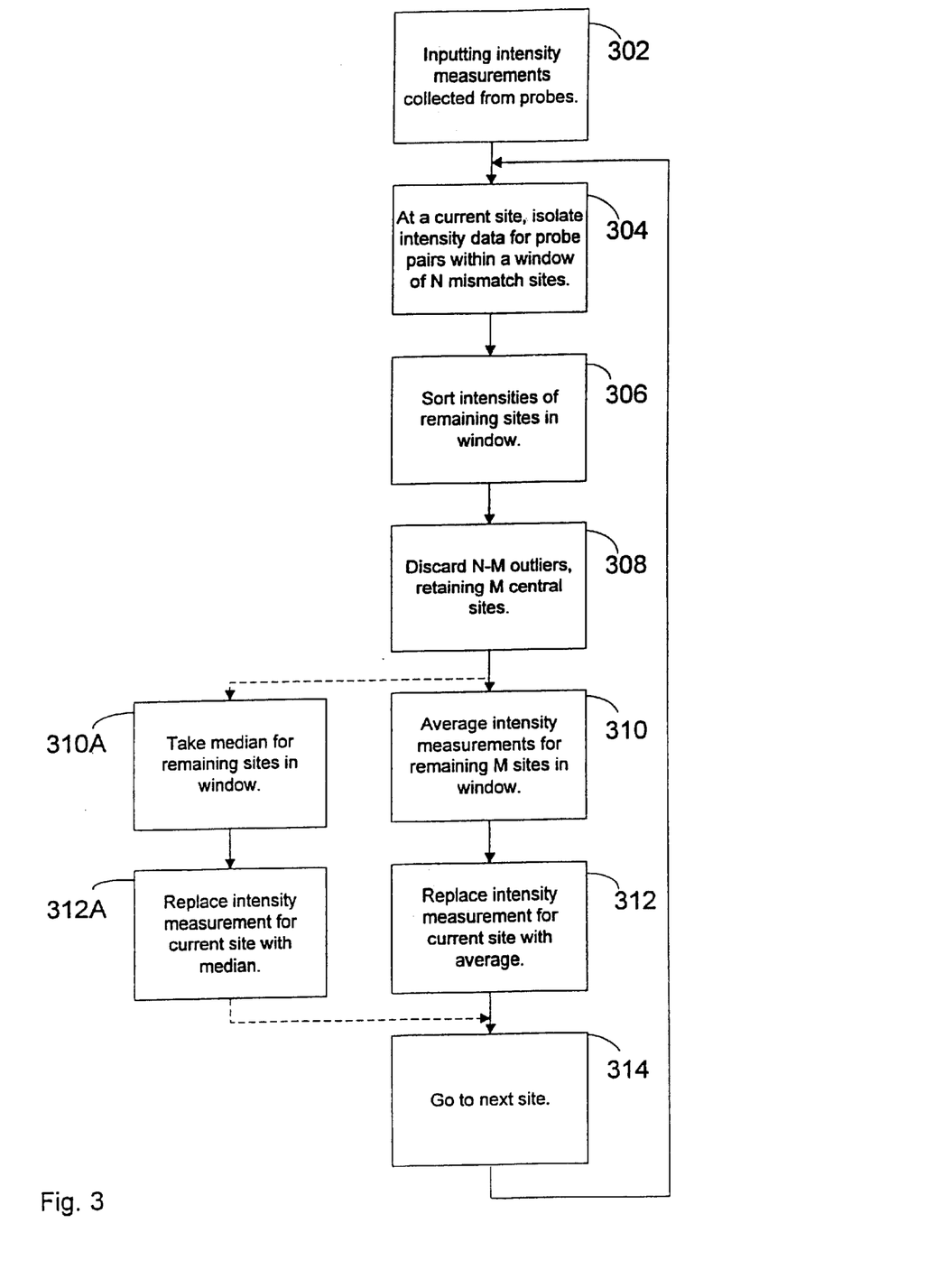
FIG. 3 is a flowchart describing steps of analyzing hybridization data using a non-linear filter according to one embodiment of the present invention.

FIG. 3 is a flowchart describing steps of processing hybridization measurements using a non-linear filter according to one embodiment of the present invention. The procedure of FIG. 3 may be applied, e.g., to the PM hybridization intensities, to the MM hybridization intensities, to the differences between PM and MM intensities for successive probes, to the ratios of PM and MM intensities for successive probes, or any combination of these measurements.

At step 302, the procedure accepts as input intensity measurements from probes used to detect the presence of a particular hybridized sequence. These measurements may be the perfect match measurements, mismatch measurements, match vs. mismatch difference measurements, ratio measurements, etc. The procedure is then applied for each alignment of probe to target sequence. Each alignment may be referred to as a "site" referring, e.g., to the base on the target that is complementary to a center base of the PM and MM probes. For a currently processed site, at step 304, the procedure isolates the hybridization intensity measurements collected from probes aligning to the target within a window of N sites surrounding the current site. If the current site is less than N/2 away from the beginning or end of the target sequence, the vector of the intensity measurements of the target sequence may be 'padded' by adding interpolated values to its beginning and end. For example, in an embodiment using a linear interpolation, if N=5 and each base i has a corresponding intensity measurement denoted as $X(i)$ for i ranging from 1 to N, the padded values are $2*X(1)-X(3)$ and $2*X(1)-X(2)$ followed by the sequences, $X(1)$ to $X(N)$, followed by padded values $2*X(N)-X(N-1)$ and $2*X(N)-X(N-2)$. Note that if the probe selection scheme provides for successive probes that may vary in alignment by more than one base, the N sites will not always be contiguous ones. If more than one probe pair has been used for each alignment, averages, medians, etc. may substitute for measurements obtained from one probe or probe pair.

At step 306, the intensity measurements obtained from each of the sites within the window of N sites are ranked in order of intensity. At step 308, the measurements from the M center sites are preserved and the rest are discarded, thus eliminating outliers. Steps 306 and 308 implement one type of lowpass nonlinear filter that may be used according to the present invention. Those of skill in the art will, however, appreciate that many nonlinear filters may be employed beneficially.

At step 310, the remaining M intensity measurements are averaged together. The resulting average replaces the original intensity measurement for the site at step 312. Alternatively, at step 310A, the procedure obtains the median of the remaining M intensity measurements. Then at step 312A, the resulting median replaces the original intensity measurement of the site. Processing of the current site then being complete, the procedure continues to the next site at step 314. Steps 304 through 314 then repeat for each succeeding alignment of probe to target sequence.

Effectively, this filter averages over the local intensity, throwing out the points with the highest and lowest intensities. Using such a filter on both the PM and MM signals, peaks and rapidly oscillating noise may be substantially reduced. It has been found that in a chip having about 100 probes per gene, the number of expressed genes that may be unambiguously detected (in which most of the probes have PM>MM) increases from about 10% using the unfiltered hybridization intensity measurements to about 20% using the filtered hybridization intensity data.

Figure 4A:
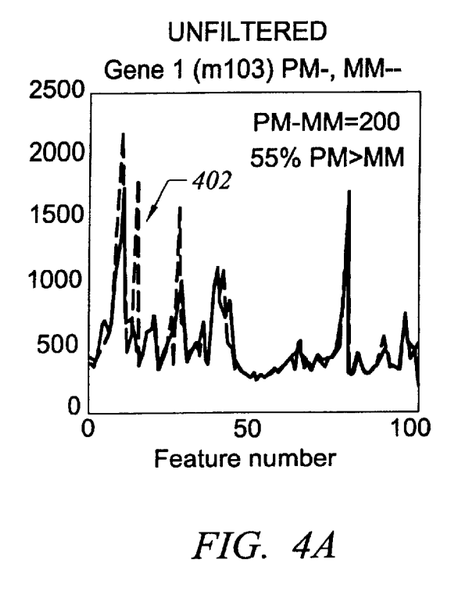
FIGS. 4A–4B depict the effects of low-pass filtering of hybridization data according to one embodiment of the present invention.
Figure 4B:
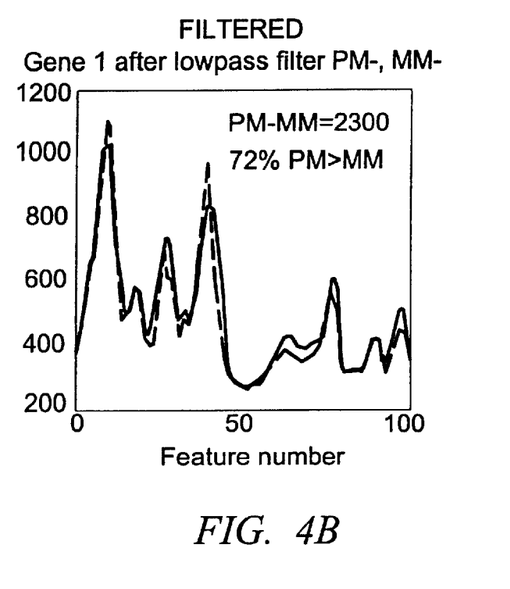

FIGS. 4A–4B depict the effects of filtering. FIG. 4A is a plot of unfiltered hybridization intensity as measured for various alignments to the target sequence. The perfect match and mismatch intensities are plotted separately. FIG. 4B shows a plot of hybridization intensity after filtering according to the present invention. Again, the perfect match and mismatch intensities have been plotted separately. Note that a spurious mismatch peak 402 in the unfiltered plot is removed in the filtered plot. Also, in the filtered data, 72% of the probe pairs exceed the PM–MM threshold and the total difference between PM and MM intensity is 2300. By contrast, in the unfiltered data only 55% of the probe pairs exceed the PM–MM threshold and the total intensity difference is only 200. Here, filtering makes the difference between detecting and not detecting gene expression.

The present invention also provides an even more sensitive system and method for detection of gene expression. This high-sensitivity detection technique takes advantage of the property that each gene has a unique recurring pattern of hybridization intensity as evaluated over probe alignment. The pattern holds over disparate tissue types, including, e.g., ovarian and breast tumors, pre- and post-nude mouse cloning, and normal tissues. These patterns, herein referred to as gene hybridization spectra, are thought to be due to changes in the hybridization efficiency resulting from variations in probe sequence. This gene hybridization spectrum may be understood as a distinct signature of each gene.

Figure 5:
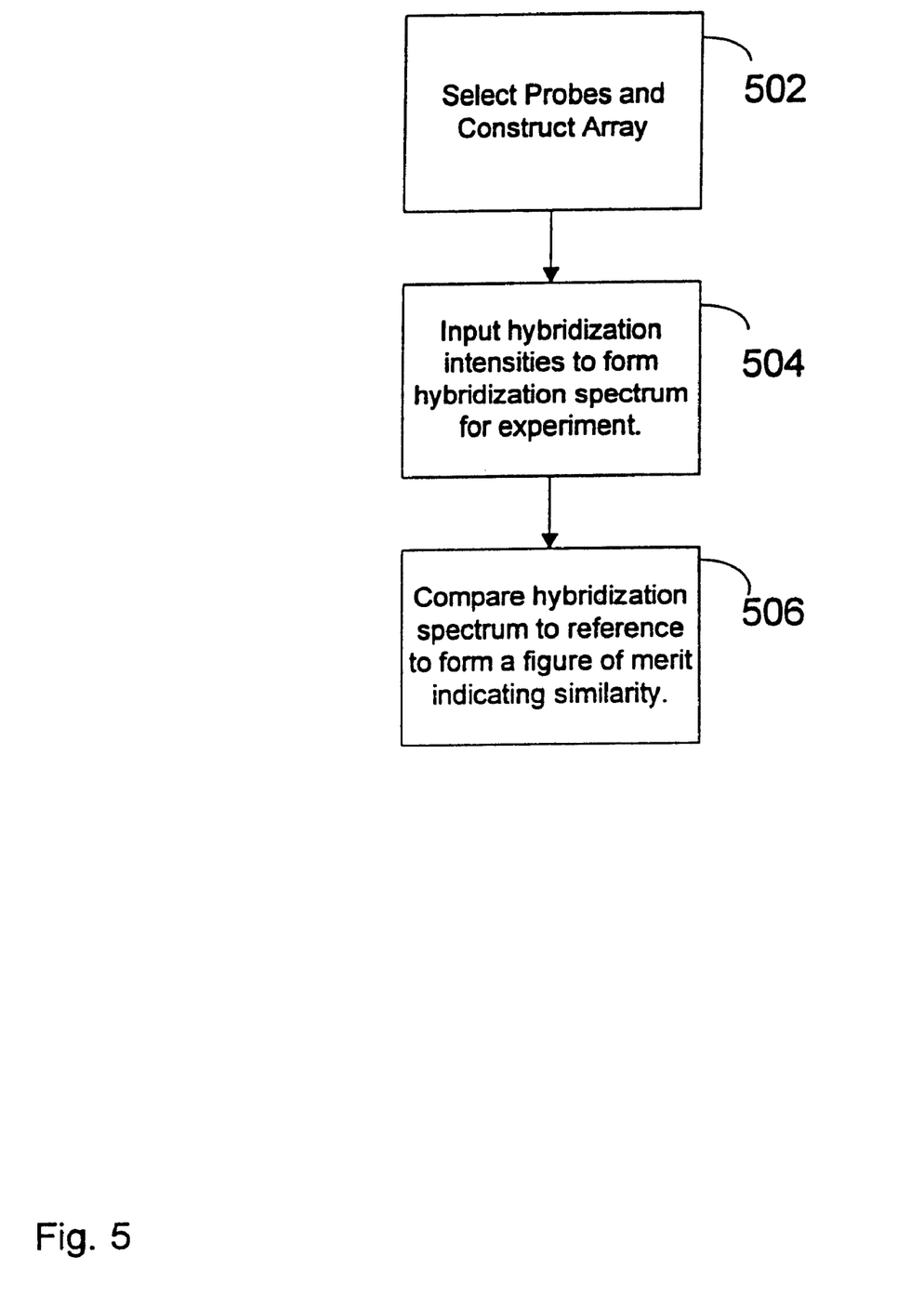
FIG. 5 is a flowchart describing steps of determining expression by use of hybridization spectra according to one embodiment of the present invention.

FIG. 5 is a flowchart describing steps of determining an expression using hybridization spectra according to one embodiment of the present invention. At step 502, probes are selected for optimal detection of gene expression. Details of step 502 will be discussed more fully below. At step 504, a hybridization spectrum may be formed from intensity measurements for probes from a particular experiment. In the presently preferable embodiment, intensities are first filtered in accordance with the steps depicted in FIG. 3 in order to remove spikes, prior to forming the hybridization spectrum. In one embodiment, this spectrum includes the intensity measurements for successive PM probes complementary to successive mRNA subsequences of the sequence along the gene. MM probe measurements may also be included or one may use difference or ratio measurements for successive probe pairs. The presently preferable embodiment forms the hybridization spectrum using the intensity difference between PM and MM. The hybridization spectrum may also be obtained by averaging intensities over many sets of identical probes on the same chip or by averaging intensities obtained from many chips.

At step 506, this hybridization spectrum is compared to a reference hybridization spectrum to determine whether or not a given gene or EST has been expressed. The reference hybridization spectrum may be the hybridization spectrum formed from intensity measurements on probes that have been exposed to a sample that is known to include mRNA indicative of gene expression. Alternatively, the reference hybridization spectrum may represent an average of measurements made on many samples known to have the expressed gene. The comparison may be to a library of reference hybridization spectra for different genes so that one experiment may be used to measure expression of many genes.

In one embodiment, a result of the comparison is a first numerical indicator of similarity between the newly formed hybridization spectrum and the reference spectrum. A second numerical indicator may give a measure of the ratio of the level of abundance of the mRNA in the new experiment to the level in the reference.

Any pattern matching algorithm can be used to perform the comparison. In one embodiment, linear regression is used. Assume that Y is the newly formed hybridization spectrum and that X is a reference hybridization specturm. The linear regression algorithm finds the best linear relation between the signals, Y=a*X+b. Here 'a' is a linear fit coefficient that gives the ratio of the level of abundance of mRNA in the new experiment to the level of the reference.

The linear regression algorithm further gives a regression coefficient r, which has a value between −1 and 1. A magnitude of r being close to 1 means a perfect linear correlation between the two spectra. When r is close to zero, that means the two spectra are completely uncorrelated. The regression coefficient thus serves as an indicator of whether a particular gene or EST is expressed.

It has been found that for a gene chip having about 100 probe pairs per gene, comparing different genes in the same experiment gives a regression coefficient of less than 0.2, indicating that the hybridization spectra of different genes are uncorrelated. When comparing the hybridization spectra of the same gene from different experiments, one obtains regression coefficients of greater than 0.8 for more than 90% of the genes. The increased sensitivity of this technique is due to the fact that the comparison takes into account all of the intensity information and not just a mean difference or some other value that attempts to represent the intensity results for all of the probes.

One may employ this hybridization spectrum evaluation technique to evaluate the quality of cDNA libraries by comparing the hybridization spectra of cDNA samples to reference spectra taken from samples of known quality. Another application would be to compare spectra to detect mutations or call bases. The reference hybridization spectrum would represent the wild type. Localized differences between the reference hybridization spectrum and the hybridization spectrum from a new experiment would represent point mutations. By comparing a new hybridization spectrum based on sample having, e.g., one unknown base, to four reference spectra collected from samples having each of the four possible bases at that position, one can call the base based on the closest matching of the four reference spectra. Again, the matching here may be based on a measure of localized differences such as e.g., mean square error, rather than an overall linear regression. To measure local differences one can perform the linear regression procedure over a small section of spectrum corresponding to the mutation point.

A modification of the above technique would be to group genes or ESTs together into families based on their hybridization spectra. Hybridization spectra are formed based on samples that express a known assortment of genes or ESTs. Those spectra that correlate with each other closely based on any pattern matching technique including the linear regression procedure outlined above are designated to be part of the same family. A family here is a group of genes or ESTs that have similar hybridization spectra.

At step 502, the design of probe arrays and probe selection strategies may be optimized to take advantage of the hybridization spectrum approach to detecting gene expression. A goal is to provide a sufficient number of probes so that each gene tested by a given array will have a detectable unique hybridization spectrum while maximizing the number of genes detectable with the available probes on an array.

Within the spectrum for a particular gene, each probe may be thought to have either a high (H) or low (L) hybridization efficiency. Thus a spectrum may be expressed as a string of H's and L's, e.g., "HLLHHHHL . . . ." If there are k probes per gene, there are $2^k$ distinct sequences of high and low intensities. Thus, for N genes, it may be sufficient to have of order of $k=\log_2 N$ probes per gene in order to have a detectably distinct pattern for each gene. Of course, the probes should then be selected to give a unique pattern for the gene.

Table 1 gives a minimum number of probes per gene for various numbers of genes in an array.

TABLE 1

| Number of Genes in Array | Number of Probes per Gene |
|---|---|
| $10^2$ | 7 |
| $10^3$ | 10 |
| $10^4$ | 14 |
| $10^5$ | 17 |
| $10^6$ | 20 |

Adding more probes per gene will improve performance but only up to a point beyond which addition of further probes per gene does not add performance but only reduces the number of genes that a given array can detect.

In the foregoing specification, the invention has been described with reference to specific exemplary embodiments thereof. It will, however, be evident that various modifications and changes may be made thereunto without departing from the broader spirit and scope of the invention as set forth in the appended claims and their fill scope of equivalents. For example, it will be understood that wherever "expression level" is referred to, one may substitute the measured concentration of any compound. Also, wherever "gene" is referred to, one may substitute the term "expressed sequence tag."

What is claimed is:

1. A method for analyzing a sample nucleic acid sequence comprising:

providing a plurality of hybridization intensities of probes including exposing said probes to said sample nucleic acid sequence, said probes including pairs of perfect match and mismatch probes, each pair including a perfect match probe perfectly complementary to a subsequence of said nucleic acid sequence and a mismatch probe having at least one base mismatch with said particular subsequence;

applying a non-linear low-pass filter to said plurality of hybridization intensities, wherein applying the non-linear filter includes averaging hybridization intensities of perfect match probes over subsequences aligned to a particular base position and subsequences aligned to surrounding base positions, excluding outlying hybridization intensities; and comparing pairs of relative hybridization intensities, wherein comparing pairs of said relative hybridization intensities determines an expression of a gene specified by said sample nucleic acid sequence.

2. The method of claim 1 wherein applying a non-linear filter comprises:

for a particular base position, averaging hybridization intensities of mismatch probes over subsequences aligned to said particular base position and subsequences aligned to surrounding base positions, excluding outlying hybridization intensities.

3. A method for analyzing a sample nucleic acid sequence comprising:

providing a plurality of hybridization intensities of probes including exposing said probes to said sample nucleic acid sequence, said probes including pairs of perfect match and mismatch probes, each pair including a perfect match probe perfectly complementary to a subsequence of said nucleic acid sequence and a mismatch probe having at least one base mismatch with said particular subsequence;

applying a non-linear low-pass filter to said plurality of hybridization intensities;

comparing pairs of relative hybridization intensities, wherein comparing pairs of said relative hybridization intensities determines an expression of a gene specified by said sample nucleic acid sequence;

evaluating relative hybridization intensities for a plurality of subsequences by comparison of hybridization intensities between perfect match and mismatch probes in individual ones of said pairs, wherein applying the non-linear filter comprises for a particular base position, averaging relative hybridization intensities over subsequences aligned to said particular base position and subsequences aligned to surrounding base positions, excluding subsequences having outlying relative hybridization intensities.

4. A method for analyzing a sample nucleic acid sequence comprising:

providing a plurality of hybridization intensities of probes including exposing said probes to said sample nucleic acid sequence, said probes including pairs of perfect match and mismatch probes, each pair including a perfect match probe perfectly complementary to a subsequence of said nucleic acid sequence and a mismatch probe having at least one base mismatch with said particular subsequence;

applying a non-linear low-pass filter to said plurality of hybridization intensities, wherein applying the non-linear filter includes obtaining a median of hybridization intensities of perfect match probes of subsequences aligned to a particular base position and subsequences aligned to surrounding base positions, excluding outlying hybridization intensities; and comparing pairs of relative hybridization intensities, wherein comparing pairs of said relative hybridization intensities determines an expression of a gene specified by said sample nucleic acid sequence.

5. A method for analyzing a sample nucleic acid sequence comprising:

providing a plurality of hybridization intensities of probes including exposing said probes to said sample nucleic acid sequence, said probes including pairs of perfect match and mismatch probes, each pair including a perfect match probe perfectly complementary to a subsequence of said nucleic acid sequence and a mismatch probe having at least one base mismatch with said particular subsequence;

applying a non-linear low-pass filter to said plurality of hybridization intensities, wherein applying the non-linear filter includes obtaining a median of hybridization intensities mismatch probes of subsequences aligned to a particular base position and subsequences aligned to surrounding base positions, excluding outlying hybridization intensities; and comparing pairs of relative hybridization intensities, wherein comparing pairs of said relative hybridization intensities determines an expression of a gene specified by said sample nucleic acid sequence.

6. A method for analyzing a sample nucleic acid sequence comprising;

providing a plurality of hybridization intensities of probes including exposing said probes to said sample nucleic acid sequence, said probes including pairs of perfect match and mismatch probes, each pair including a perfect match probe perfectly complementary to a subsequence of said nucleic acid sequence and a mismatch probe having at least one base mismatch with said particular subsequence;

applying a non-linear low-pass filter to said plurality of hybridization intensities;

comparing pairs of relative hybridization intensities, wherein comparing pairs of said relative hybridization intensities determines an expression of a gene specified by said sample nucleic acid sequence;

evaluating relative hybridization intensities for a plurality of subsequences by comparison of hybridization intensities between perfect match and mismatch probes in individual ones of said pairs, wherein applying the non-linear filter comprises for a particular base position, obtaining a median of relative hybridization intensities over subsequences aligned to said particular base position and subsequences aligned to surrounding base positions, excluding subsequences having outlying relative hybridization intensities.

* * * * *